United States Patent [19]

Hund et al.

[11] Patent Number: 5,328,371
[45] Date of Patent: Jul. 12, 1994

[54] DENTAL IMPLANT

[75] Inventors: Walter Hund, Oberkirch-Stadelhofen; Freimut Vizethum, Schwetzingen, both of Fed. Rep. of Germany

[73] Assignee: Friatec Aktiengesellschaft, Mannheim, Fed. Rep. of Germany

[21] Appl. No.: 136,367

[22] Filed: Oct. 15, 1993

[30] Foreign Application Priority Data

Oct. 23, 1992 [DE] Fed. Rep. of Germany ....... 4235801

[51] Int. Cl.$^5$ .............................................. A61C 8/00
[52] U.S. Cl. ................................................. 433/173
[58] Field of Search ............... 433/169, 173, 174, 175, 433/176

[56] References Cited

U.S. PATENT DOCUMENTS 2,854,746 10/1958 Lester et al. ...................... 433/169
4,324,550 4/1982 Reuther et al. .................... 433/169
5,213,500 5/1993 Salazar .............................. 433/169

Primary Examiner—Cary E. O'Connor
Attorney, Agent, or Firm—Evenson, McKeown, Edwards & Lenahan

[57] ABSTRACT

A dental implant comprising an implant body which can be anchored in the jawbone and a superstructure portion which can be inserted at least partially in a recess of the implant body and which is fixed in place by a holding screw. The recess in the implant body is provided with a first contact surface and the superstructure portion is provided with an associated second contact surface for securing the superstructure against rotation relative to the implant body in a durable and functionally reliable manner such that play between the implant body and the superstructure is avoided. The superstructure portion is provided with at least one slot extending from its free end to the vicinity of the second contact surface and with a tapered portion disposed radially inwardly of the contact surfaces. When the holding screw is screwed in, a cam surface associated with the holding screw engages the tapered portion such that the superstructure portion is spread radially and the first and second contact surfaces firmly contact each other.

12 Claims, 3 Drawing Sheets

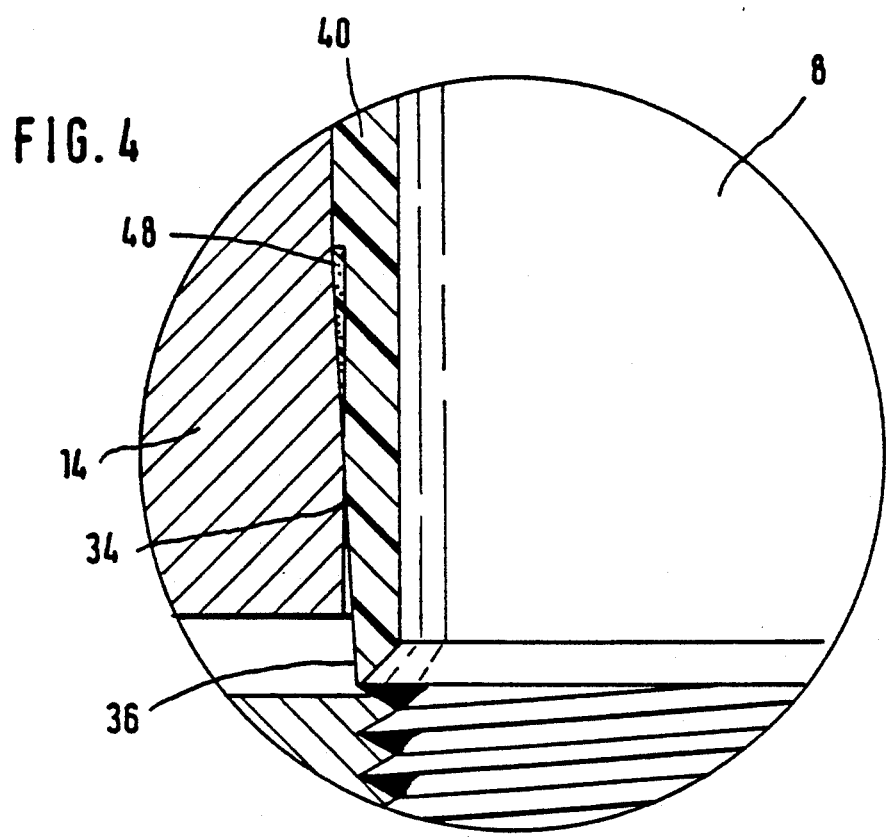
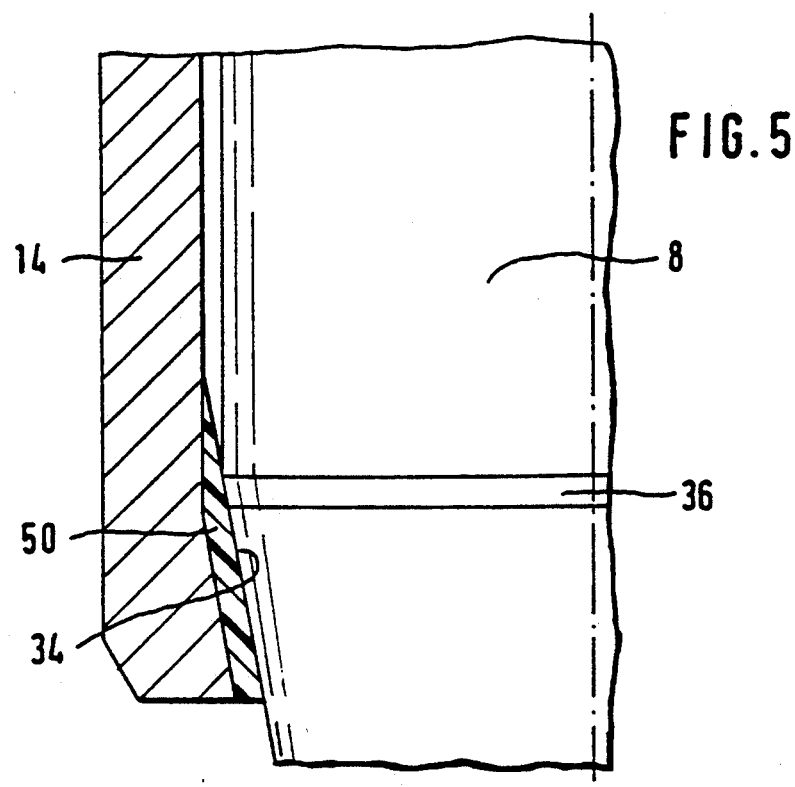

DENTAL IMPLANT

BACKGROUND OF THE INVENTION

This invention relates to a dental implant comprising an implant body which can be anchored in a jawbone and a superstructure portion which can be inserted at least partially in a recess arranged on the coronal end of the implant body and which can be fastened in the implant body by a holding screw, wherein the recess comprises at least one first contact surface which contacts an associated second contact surface on the superstructure in order to secure the parts against relative rotation.

Schulte et al., U.S. Pat. No. 5,199,873 discloses a dental implant which has an implant body that can be anchored in the jawbone. At the coronal end, the implant body has a recess in which a superstructure portion can be partially inserted and can be fastened by means of a holding screw. In order to affix the superstructure portion so that it cannot rotate relative to the implant body, at least one contact surface is provided in the recess, against which an associated contact surface of the superstructure portion rests in a form-keyed manner. These contact surfaces are advantageously designed in the shape of a hexagon and produce a rotation stop while being easy to handle. However, two-phase dental implants of this type exhibit rotational play at the connection between the superstructure portion and the implant body, which play leads to inaccurate positioning. Furthermore, such relative movements may lead to loosening of the holding screw as well as to frictional corrosion in the gap area between the superstructure and the implant body. For manufacturing reasons, a fit between the superstructure portion and the implant body that is free from play cannot be achieved, because otherwise it would be impossible to insert the superstructure portion in the implant body. It has been found in practice that, even if the superstructure portion and the implant body are manufactured with a high precision form-keyed hexagon connection, a play of from 2 to 3 degrees of angle about the longitudinal axis may occur. In addition, in dental implants of this type, a defined axial positioning of the superstructure portion with respect to the implant body is essential. Thus, conical fittings, which are known not to enable precise axial positioning, cannot be used to establish a play-free connection between the superstructure portion and the implant body.

Furthermore, Reuther et al, Swiss Patent No. CH 642,838 discloses a dental implant which comprises an implant body which can be inserted into the jawbone, a plastic bearing and a superstructure portion or implant carrier. The plastic bearing is screwed into a conical bore of the implant body and contains a coaxial internal bore with a thread. A threaded pin on the superstructure portion is screwed into this internal bore. Plastic deformation of the plastic bearing results in a pseudo-conical clamping, so that a tight connection can be established by screwing the parts together. However, there is nothing to prevent relative rotation between the superstructure portion, on the one hand, and the implant body, on the other hand.

Perisse, French Patent No. FR 2,663,836 discloses a dental implant having a hollow, substantially cylindrical implant body. The apical end of the superstructure portion, which can be inserted into the implant body, is formed with a slot and contains an internal through-bore which is filled with balls or the like and which converges at the apical end so that the balls cannot pass through the slot. Pressure can be applied to the balls by means of a screw which is arranged in the through bore at the coronal end of the superstructure portion, so that the superstructure portion is spread apart at the apical end and is pressed in the recess of the implant body. Thus, the superstructure portion is affixed to the implant body without a holding screw screwed into the implant body and without any means for preventing relative rotation.

Caracciolo, U.S. Pat. No. 4,588,381 discloses an implant comprising a tube-shaped implant body. At the apical end, the implant body is provided with slots, and the internal bore is designed in a conically tapering manner. When the superstructure portion is screwed in, the implant body is spread at the apical end in order to anchor the implant. In this case, there is no fixing due to compression, like that achieved when using a holding screw. Also, it is not possible to precisely position the superstructure portion in the implant body in this manner.

Fath, Published German Patent Application No. DE 4,000,112 discloses a dental implant with an implant body which again has a slotted design on its apical end and which is provided with a central recess. A screw can be screwed into this recess, whereby the tip of the screw spreads open the end of the implant body as it is screwed in and anchors the implant in the bone. This implant does not provide any advantageous teachings with regard to fastening the superstructure to the implant body or to fixing their positions and securing them against relative rotation.

SUMMARY OF THE INVENTION

It the object of the present invention to provide an improved dental implant.

Another object of the invention is to provide a dental implant design which assures that the superstructure cannot rotate with respect to the implant body.

A further object of the invention is to provide a dental implant in which the superstructure is secured to the implant body in a durable and functionally reliable manner.

An additional object of the invention is to provide a dental implant in which there is no rotational play between the superstructure and the implant body.

It is also an object of the present invention to provide a dental implant which is compatible with previously used implant components.

Yet another object of the invention is to provide a dental implant which avoids play between the superstructure and the implant body and which can be produced at a low additional manufacturing cost.

A still further object of the invention is to provide a dental implant which avoids rotational play and yet enables precise axial positioning of a superstructure portion.

These and other objects of the invention are achieved by providing a dental implant comprising an implant body which has root and crown ends and which can be anchored in a patient's jawbone; a superstructure portion having a free end which can be inserted at least partially into a recess in the crown end of the implant body; and a holding screw extending through said superstructure portion and engaging mating threads in said recess of the implant body for fastening the superstructure portion to the implant body; in which the recess in the implant body is provided with at least one first contact surface; and the superstructure portion is provided with an associated second contact surface for each first contact surface, and with at least one slot extending from said free end to the vicinity of said second contact surface(s), and with a smaller diameter portion disposed radially inwardly of the second contact surface(s); and in which a cam member is associated with the holding screw such that when the holding screw is screwed into the implant body, the cam member engages the smaller diameter portion of the superstructure portion and radially spreads the superstructure portion in such a way that the second contact surface(s) are urged against the associated first contact surface(s), and the superstructure portion is secured against rotation relative to the implant body.

The dental implant of the invention is characterized by a functionally appropriate construction and ensures in a confident and durable manner the rotational stability of the superstructure portion relative to the implant body. In the area of the contact surfaces, the superstructure portion is formed with a slot, and the screwing-in of the holding screw causes the superstructure to be deformed in such a manner that at least one of the contact surfaces of the center part directly contacts the associated contact surface of the implant body in a form-locking manner. With respect to this radial deformation of the superstructure portion, its interior surface, which is provided with a smaller diameter portion and which is preferably constructed as an annular shoulder or a cone, when the holding screw is screwed in, engages an associated cam surface of the holding screw or of an additional sleeve in such a manner that, when the holding screw is screwed in more, not only the axial tensile stress but, at the same time, the play-compensating expansion force is achieved.

The cam surface and/or the tapered surface may be made of a deformable material. This type of material is softer than the material of the holding screw or of the superstructure portion and enables the superstructure portion to be fastened to the implant body with an axial prestress or compression, and the superstructure portion nevertheless to expand radially in order to eliminate the play. Thus, for example, the area of the cam surface consists of the mentioned softer material and when it comes into contact with the smaller diameter surface of the superstructure portion, this contact does not preclude further screwing-in of the holding screw. Any gap which may possibly still exist between the face of the implant body and the associated annular shoulder of the recess may be closed by a further screwing-in of the holding screw until finally the required compression is built up between the face and the annular shoulder in order to achieve a connection which is tight with respect to bacteria. Because a deformable material is used in the area of the cam surface or of the smaller diameter portion, when the cam surface and the smaller diameter portion contact one another, further screwing-in and axial movement of the screw are not prevented. The material experiences a plastic or elastic deformation in such a way that, despite the contact between the cam surface and the tapered surface, the holding screw can be screwed in more, and the superstructure portion is spread radially at the same time. Thus, for example, the cam surface may be a component of a sleeve made of plastic or may, by means of a coating, be injection-molded or vulcanized in an annular shape or in the form of cams onto the outer surface of the holding screw. Correspondingly, the entire smaller diameter surface of the of the superstructure portion may be made of a material that is softer than the material of the rest of the superstructure portion, such as a plastic material or a softer metal.

The formation of the slot, which preferably is situated in an axial plane, in the superstructure portion requires only minimal additional manufacturing expenditures in comparison to a conventional superstructure portion. The implant body proper may be maintained in an unchanged manner, the slotted superstructure portion of the invention being fully compatible with the conventional implant bodies used in the past.

Further features and preferred embodiments of the dental implant according to the invention are described hereinafter.

BRIEF DESCRIPTION OF THE DRAWINGS

The invention will be described in further detail with reference to preferred embodiments illustrated in the accompanying drawing figures in which

FIG. 4 is an enlarged detail view of the area IV of FIG. 1; and

FIG. 5 is a schematic view of a modified embodiment of the aforementioned detail IV.

DETAILED DESCRIPTION OF PREFERRED EMBODIMENTS

Figure 1:
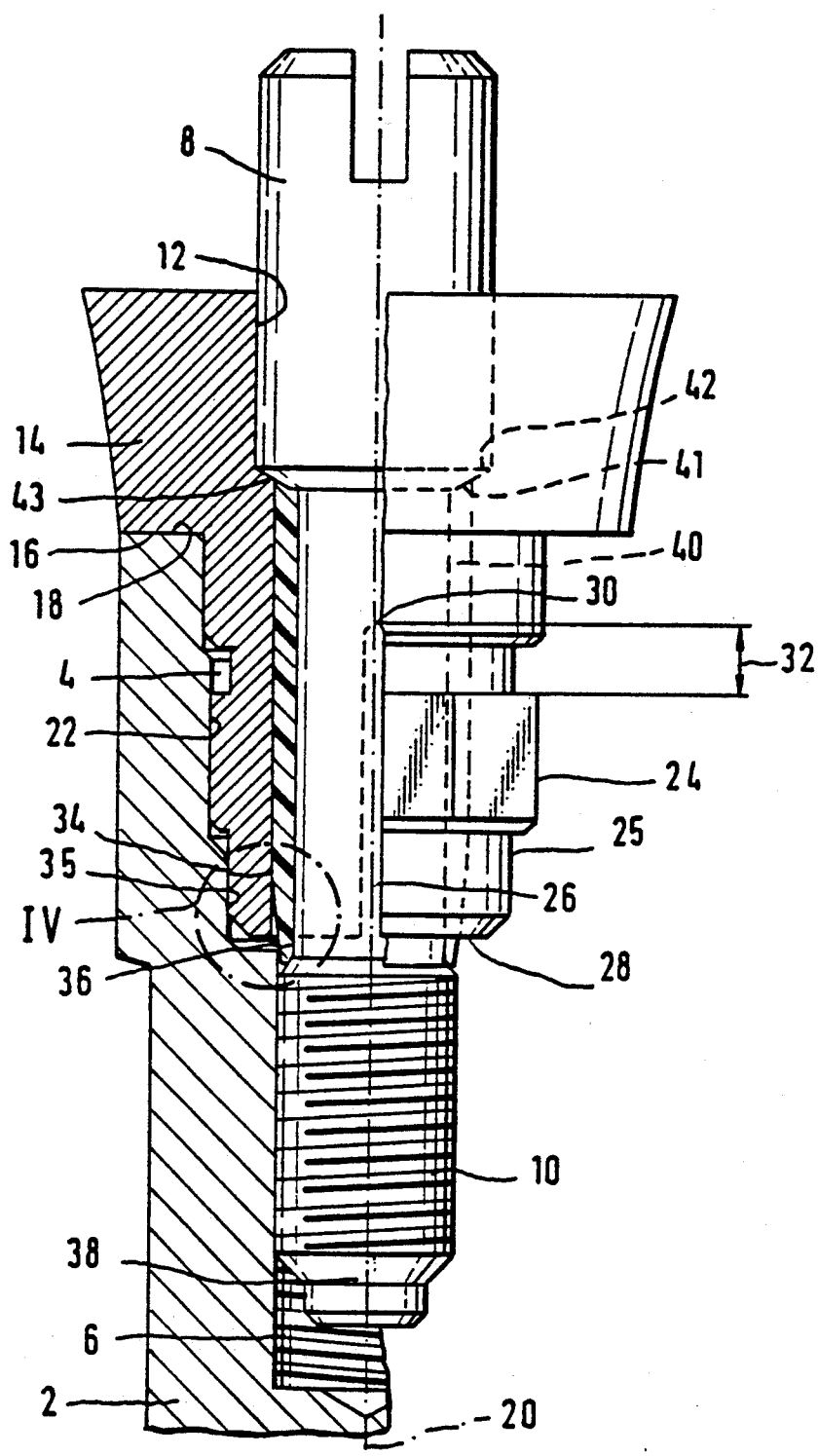
FIG. 1 is a partial longitudinal sectional view of the dental implant of the invention.

FIG. 1 illustrates in partial axial section an implant body 2 which has a recess 4 on the coronal end. The implant body 2 is shown only partially and, according to FIG. 1, may be constructed in the downward direction to the apical end partially as stepped cylinder or a stepped screw. Coaxially to the recess 4 and adjoining it, the implant body 2 has an internal thread 6 into which a holding screw 8 is screwed by means of an external thread 10.

The holding screw 8 extends through an internal-bore 12 of a superstructure portion 14 which is partially inserted into the recess 4 of the implant body 2. The internal bore 12 is constructed as a through-bore so that the holding screw 8 may be guided through so far that the mentioned external thread 10 can be screwed into the internal thread 6 which axially adjoins the recess 4 and the part of the superstructure 14 anchored in it. The internal bore 12 of the superstructure portion 14 is arranged coaxially with respect to the recess 4 and/or the internal thread 6 of the implant body 1.

The superstructure portion 14 rests with an annular shoulder 16 firmly compressed against the coronal face 18 of the implant body 2, and a defined axial alignment is ensured in the direction of the longitudinal axis 20 of the superstructure portion 14 with respect to the implant body 2. Compressive force is applied by means of the holding screw 8 screwed into the implant body 2, and a gap-free connection between the superstructure portion 14 and the implant body 2 is ensured which is tight with respect to bacteria. As can be seen in the drawing, the axial face 18 extends to the outer circumference of the implant body 2, and likewise the annular shoulder 16 extends to the outer surface of the superstructure portion 14. The invention assures a connection under compression which is tight and gap-free in combination with secure prevention of rotation as explained hereinafter.

Within the recess 4, the implant body 2 has first contact surfaces 22 which are aligned in parallel to the longitudinal axis 20. Advantageously, six of these contact surfaces 22 in the form of a hexagon are arranged symmetrically with respect to the longitudinal axis 20. Correspondingly, the superstructure portion 14 has second contact surfaces 24 which are situated opposite and associated with the first contact surfaces 22 in order to secure the superstructure portion 14 against rotation by means of a form-locking. However, because of indispensable manufacturing tolerances, there is always a certain play between the first contact surfaces 22 and the second contact surfaces 24.

The first contact surfaces 22 as well as the second contact surfaces 24 are preferably arranged essentially parallel to the longitudinal axis 20, but within the scope of this invention, they may also have a different alignment with respect to the longitudinal axis 20. The mutually opposite first contact surfaces 22 and second contact surfaces 24 are advantageously disposed in essentially axial planes, such that a line normal to the plane is essentially perpendicular to the longitudinal axis 20. The important thing is that in conjunction with the means described hereinafter for compensating for play, when the holding screw 8 is screwed in, the associated contact surfaces 22 and 24 are at least partially pressed against one another, so that the superstructure portion 14 and the implant body 2 are mutually fixed and secured against rotation relative to each other.

In order to enable the superstructure portion 14 to compensate for play, it is provided with at least one slot 26 which extends from the free end 28 through the area of the second contact surfaces 24. The slot 26 extends from the outer surface of the superstructure portion 14 continuously to its interior surface. Advantageously, a second slot is correspondingly arranged in the same axial plane as the slot 26, which is visible here, behind the plane of projection. These two slots are placed in a simple manner in the superstructure portion 14 during the same operation and permit radial expansion of the superstructure portion 14 in the area of its contact surfaces 24. The base 30 of the slot 26 extends a predetermined distance 32 in the axial direction beyond the end of the second contact surfaces 24. This advantageously assures an essentially flat, form-locking contact between the first and the second contact surfaces after the spreading of the superstructure portion 14.

The superstructure portion 14 has a smaller diameter internal surface portion 34, in which case the inside diameter in the area of the free end 28 is smaller than is the inside diameter in the area surrounded on the outside by the second contact surfaces 24. In this case, this smaller diameter surface 34 is constructed as a collar, the edges advantageously being conically sloped or provided with a bevel. The holding screw 8 has a cam surface 36 which is associated with the smaller diameter 34. This cam surface 36 is advantageously constructed as a conical surface whose vertex 38 faces the apical end. When the holding screw 8 is screwed in, the cam surface 36 engages the smaller diameter surface 34, and radially directed force components are exerted against the superstructure portion 14. As the holding screw 8 is screwed in more, the slot 26 permits the superstructure portion to spread radially so that the existing play between the first and second contact surfaces will disappear. The radially mutually opposite contact surfaces 22 and 24 rest at least partially against one another in a form-locking manner so that relative movements about the longitudinal axis 20 are durably prevented in a functionally reliable manner. Since the annular shoulder 16 of the superstructure portion 14 and the end face 18 of the implant body 2, which are situated opposite one another in the axial direction, are pressed firmly and tightly against one another when the holding screw 8 is screwed in, an exact axial alignment of the superstructure portion 14 with respect to the implant body 2 is assured at the same time.

In the axial direction between the second contact surfaces 24 and the free end 28, the superstructure portion 14 has a cylindrical area 25. In accordance with the invention, the diameter of this cylindrical area is smaller than the inside diameter of the radially opposite area 35 of the recess 4. Within the scope of the invention, the difference of diameters of the areas 25 and 35 is selected such that the holding screw 8 can be screwed in and the slotted superstructure portion 14 spread unhindered until the mutually associated contact surfaces 22 and 24 are pressed against one another.

One preferred embodiment comprises a sleeve 40 shown by broken lines. The holding screw 8 extends through the sleeve 40 and has a correspondingly reduced outside diameter. In this embodiment, the cam surface 36 is not an integral component of the holding screw 8, but when the holding screw 8 is screwed into the implant body 2, the radial force components due to the cam surface 36 nevertheless effectively spread the superstructure portion 14. The axial end face 41, shown at the top of FIG. 1, of sleeve 40 rests against a collar 42 of the holding screw 8 or its screw head. Advantageously, the holding screw 8 comes to rest by way of the collar 42 against a annular shoulder 43 of the superstructure portion 14. When the holding screw 8 is tightened in the implant body 2, an axial compressive force is applied by way of the annular shoulder 43 to the superstructure portion 14 which results in gap-free contact between the superstructure portion 14 and the axial face 18 of the implant body that is tight with respect to bacteria. Thus, when the holding screw 8 is screwed in, an axial force first affects the sleeve 40 until the cam surface 36 engages the smaller diameter surface 34, and subsequently the radial force components act upon the superstructure portion 14 and spread it.

The sleeve 40 is preferably deformable in such a manner that, on the one hand, the aforedescribed widening of the superstructure portion 14 will take place but that, on the other hand, the ability to precisely axially position of the superstructure portion 14 with respect to the implant body 2, which is needed in view of manufacturing tolerances, will be virtually unimpaired. If there is still a relatively large gap between the axial face 18 and the annular shoulder 16 of the superstructure portion 14 when the cam surface 36 engages the smaller diameter surface 34, then the superstructure portion 14 will then spread until the first and second contact surfaces rest against one another without play. As the screwing-in continues, the sleeve 40 will be deformed until there is no gap between axial face 18 and annular shoulder 16, and the axial bracing with the desired compressive force is achieved between the superstructure portion 14 and the implant body 2. For the sake of completeness, it should be mentioned that in this embodiment the outside diameter of the external thread 10 is naturally smaller than the inside diameter of the sleeve 40 so that the holding screw 8 can be extended through the sleeve 40 in the indicated manner.

In the aforedescribed embodiment, the sleeve 40 is made of a softer material than the superstructure portion 14 and/or the holding screw 8, reference being made here particularly to plastic. After the cam-surface 36 engages the smaller diameter surface 34, when the holding screw 8 is screwed in further, the material is plastically or elastically deformed, in which case partial areas are displaced along the outer surface of the sleeve. A pressure buildup occurs in this case which results in radial spreading of the superstructure portion in this area. Within the scope of the invention, the sleeve 40 may be designed as a separate component which is slid onto the screw just as well as by the coating of the outer surface of the holding screw integrally with this holding screw. The cam surface may also be designed in the form of nubs, projections or the like which are distributed along the circumference of the holding screw and which can be deformed when they contact the smaller inner diameter portion of the superstructure portion as described above and cause the superstructure portion to spread radially. Furthermore, within the scope of the invention, the smaller diameter portion may also be formed of a correspondingly softer material, in which case, in addition to the aforedescribed construction as a collar, a different geometry, such as particularly nubs, projections or the like, may also be provided.

Figure 2:
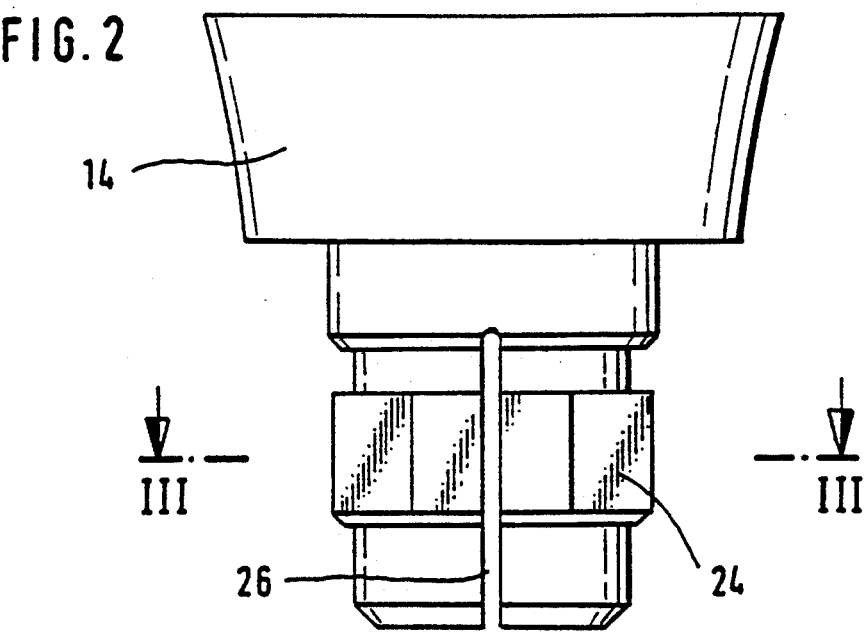
FIG. 2 is a view of the superstructure portion of the implant of FIG. 1.
Figure 3:
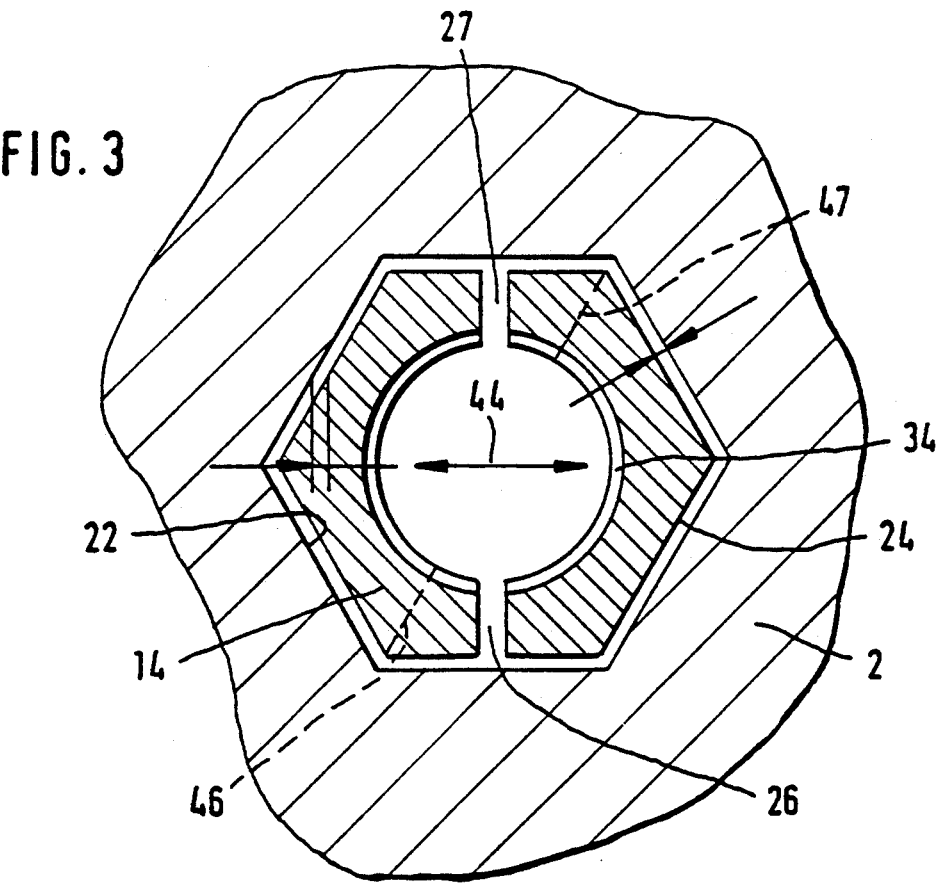
FIG. 3 is a sectional view taken along section line III—III of FIG. 2.

In a lateral view and in an enlarged view in a radial plane along the intersection line III, FIGS. 2 and 3 show the superstructure portion 14. FIG. 3 clearly shows the first and second contact surfaces 22 and 24 of the implant body 2 and of the superstructure body 4 which are constructed in the shape of a hexagon. The two slots 26, 27, which can clearly seen in the drawing, are each arranged in the center of one of the second contact surfaces 14. It should be pointed out that in order to illustrate the relationships, the play between the first and second contact surfaces 22 and 24 is shown in the drawing in an exaggerated manner. In conventional dental implants, however, a play of only 0.01 to 0.02 mm enables the superstructure portion 14 to rotate from 2 to 3 degrees of angle around its longitudinal axis 20 with respect to the implant body 2. When the cam surface 36 comes to rest against the smaller diameter portion 34 in the above-described manner as the holding screw is screwed in, the areas of the superstructure portion 14 separated by means of the slots 26, 27 are pushed radially apart in the direction of the double arrow 44, with the result that the play becomes zero between at least some of the contact surfaces of the superstructure portion 14 and of the implant which are associated with one another in pairs.

In FIG. 3, alternative arrangements of the two above-described slots of the superstructure portion 14 are indicated by broken lines 46, 47. These slots are now situated in the corners between two adjacent contact surfaces 24. While taking into account the angles, it is found that for this alternative embodiment the required widening is slightly larger than in the embodiment in which the slots 26, 27 each extend between the centers of two diametrically opposite contact surfaces 24.

FIG. 4 shows an enlarged detail view of the area of the tapered surface 34 of the superstructure portion 14 in conjunction with the conical cam surface 36 of the holding screw 8. After the cam surface 36 of the sleeve 40 made of a softer material comes into contact with the step-shaped reduced diameter portion 34, when the holding screw 8 is screwed further into the thread of the implant body, the softer, deformable material of the sleeve 4 is displaced into the space 48, and a pressure is generated which eventually causes the superstructure portion 14 to spread radially.

FIG. 5 is a schematic view of the kinematic reversal in such a manner that the cam surface 36 of the holding screw 8 is formed by a step which rests against the conically formed tapered smaller diameter surface 34 of the superstructure portion 14. The tapered smaller diameter surface 34 is formed by a layer 50 which is applied as shown in the drawing to the interior surface of the superstructure portion 14. This layer 50 is made of a deformable material which is softer than the material of the holding screw 8 with the associated cam surface 36. When the holding screw 8 is screwed in further, the layer material is displaced and/or pressure builds up in the area of the layer 50, which axially adjoins underneath the cam surface 36 as shown in FIG. 5, in order to radially spread the superstructure portion 14. It can be seen that the cam surface is produced by forming the holding screw 8 with stepped outside diameters, with the smallest diameter at the apical end. The cam surface 36 may also be provided with a small bevel corresponding to the vertex angle of the conically tapered surface 34.

The foregoing description and examples have been set forth merely to illustrate the invention and are not intended to be limiting. Since modifications of the disclosed embodiments incorporating the spirit and substance of the invention may occur to persons skilled in the art, the invention should be construed to include everything within the scope of the appended claims and equivalents thereof.

What is claimed is:

1. A dental implant comprising:
   an implant body having root and crown ends and which can be anchored in a patient's jawbone;
   a superstructure portion having a free end which can be inserted at least partially into a recess in the crown end of the implant body; and
   a holding screw extending through said superstructure portion and engaging mating threads in said recess of said implant body for fastening the superstructure portion to the implant body; wherein said recess is provided with at least one first contact surface; and wherein said superstructure portion is provided with
      an associated second contact surface for each first contact surface; and with
      at least one slot extending from said free end to the vicinity of said second contact surface(s); and with
      a smaller diameter portion disposed radially inwardly of said second contact surface(s); and wherein a cam member is associated with said holding screw such that when the holding screw is screwed into the implant body, the cam member engages said smaller diameter portion and radially spreads said superstructure portion in such a way that said second contact surface(s) are urged against the associated first contact surface(s), whereby said superstructure portion is secured against rotation relative to said implant body.

2. A dental implant according to claim 1, wherein at least one of said smaller diameter portion and said cam member is made of a deformable material.

3. A dental implant according to claim 1, wherein at least one of said smaller diameter portion and said cam member is made of a softer, more easily deformable material than said holding screw and said superstructure portion.

4. A dental implant according to claim 1, wherein said smaller diameter portion is arranged on a sleeve which surrounds said holding screw, said sleeve having an axial end face contacting an annular abutting face on said holding screw.

5. A dental implant according to claim 4, wherein said abutting face on said holding screw is an end face of a screw head.

6. A dental implant according to claim 1, wherein two diametrically opposed slots are provided in said superstructure portion, said slots extending from the free end of said superstructure portion past said second contact surface(s).

7. A dental implant according to claim 1, wherein said at least one slot extends from the free end of said superstructure portion through said second contact surface(s) and a predetermined distance beyond said second contact surface(s).

8. A dental implant according to claim 1, wherein said cam member comprises a substantially conical cam surface having a vertex end which faces the free end of said superstructure portion.

9. A dental implant according to claim 1, wherein the said smaller diameter portion comprises a substantially conical contact surface having a vertex end proximate the free end of said superstructure portion.

10. A dental implant according to claim 1, wherein the superstructure portion is provided with an annular shoulder which is compressed by said holding screw against an abutting axial end face of said implant body.

11. A dental implant according to claim 1, wherein said holding screw is screwed into said implant body such that the holding screw is under tensile stress, and a screw head on said holding screw is compressed against an annular shoulder on said superstructure portion.

12. A dental implant according to claim 1, wherein said superstructure portion is provided with at least two diametrically opposed slots arranged in an axial plane of said superstructure portion and extending from the free end past said second contact surface(s).

* * * * *